United States Patent [19]

King

[11] Patent Number: 5,648,231

[45] Date of Patent: Jul. 15, 1997

[54] MEASUREMENT OF MOLD GROWTH ON AMORPHOUS SUBSTRATES

[75] Inventor: Bruce Dexter King, Troy, Ill.

[73] Assignee: Ducoa, L.P., Highland, Ill.

[21] Appl. No.: 385,399

[22] Filed: Feb. 7, 1995

Related U.S. Application Data

[63] Continuation of Ser. No. 891,337, May 29, 1992, abandoned.

[51] Int. Cl.$^6$ .............................. C12Q 1/02; C12Q 1/18; G01N 33/53; C12M 1/00
[52] U.S. Cl. ................. 435/34; 435/4; 435/7.31; 435/807; 435/32; 435/29
[58] Field of Search ................ 435/4, 7.31, 287, 435/807, 32, 291, 29, 34

[56] References Cited

U.S. PATENT DOCUMENTS

| | | | |
|---|---|---|---|
| 3,613,308 | 10/1971 | Klein et al. | 47/17 |
| 4,600,706 | 7/1986 | Carter | 514/31 |
| 4,945,060 | 7/1990 | Turner et al. | 435/291 |
| 4,947,339 | 8/1990 | Czekajewski et al. | 364/497 |
| 5,073,503 | 12/1991 | Mee | 436/147 |

FOREIGN PATENT DOCUMENTS

| | | | |
|---|---|---|---|
| 77-35410 | 11/1977 | France | C12K 1/00 |

OTHER PUBLICATIONS

Animal Nutrition Research, Analytical Method, R881, Comparative Efficiency of Mold Inhibitors, BASF Corp., 1989.
Keeping Current, No. 898, Comparison of Mold Inhibitor Efficacy Tests, BASF Corp., Undated.
Keeping Current, Analytical Method No. 8920, Procedure for Evaluation of Mold Inhibitor Efficacy, BASF Corp., Undated.

*Primary Examiner*—Esther Kepplinger
*Assistant Examiner*—Choon P. Koh

[57] ABSTRACT

A method for rapidly determining mold growth on feed is disclosed. The method comprises placing a sample of feed containing mold spores in a closed container; maintaining an environment that will support rapid mold growth; measuring the change in concentration of oxygen and/or carbon dioxide; and correlating the concentration change with the rate of mold growth.

19 Claims, 3 Drawing Sheets

MEASUREMENT OF MOLD GROWTH ON AMORPHOUS SUBSTRATES

This is a continuation of application Ser. No. 07/891,337 filed May 29, 1992, now abandoned.

BACKGROUND OF THE INVENTION

1. Field of the Invention

This invention relates to a method and apparatus for measuring mold growth.

2. Description of Related Art

Mycotoxin contamination of foodstuffs is a common problem impacting the grain, feed, and animal industries. It is known that at least 300 different mycotoxins can contaminate cereal grains and oil seeds. Contamination of these foodstuffs can result in destruction of large quantities of grain. Additionally, since these commodities typically represent a major component of animal feeds, the threat to animal health from mycotoxin contamination is significant. Due to an increased awareness of the potential health hazards associated with mycotoxins, and recent advances in the testing of feedstuffs for the presence of mycotoxins, contamination of grains and feed by these compounds is considered one of the major problems facing the grain and animal industries. Mycotoxin contamination of foodstuffs is the result of uncontrolled growth of certain toxigenic molds. Mycotoxins are highly toxic metabolic by-products, released into the immediate environment as these molds grow. As time proceeds, the molds responsible for the production of the mycotoxins may become non-viable. However, in most cases the mycotoxins remain due to their high chemical stability.

A logical approach to minimizing mycotoxin contamination in foodstuffs is to minimize mold growth. Numerous approaches have been employed by the grain, feed, and animal industries to minimize mold growth in foodstuffs: (1) Proper use of insecticides, fertilizers, and irrigation techniques reduces greatly the probability of mold growth and mycotoxin formation in pre-harvest grain. (2) Early harvest of grain usually leads to minimal mold growth and minimal mycotoxin contamination because mold growth occurs in pre-harvest grains near the end of the growing cycle of the grain. (3) Immediate, rapid and complete drying of harvested grains retards the growth of molds in post-harvest grain. However, the drying procedures must be initiated as soon after harvest as possible, and the final moisture of the grain must be low enough to prevent mold growth. (4) Storage of grain and manufactured feeds in storage facilities that are dry, water-tight, and free of moldy and caked material assists in the prevention of mold growth and mycotoxin contamination in grain or feed stored in these storage containers. (5) Rapid use of manufactured feeds decreases the chance of mold growth during the period between feed manufacture and feed consumption. (6) The use of chemical preservatives minimizes mold growth in grain and feed, thereby minimizing the change of mycotoxin contamination in these commodities. Given the relevance and importance of mold growth to mycotoxin contamination of feedstuffs, it is obvious that an accurate method for measuring mold growth in commodities where the cultural conditions closely mimic practical or "field" conditions is imperative. This is particularly important when the efficacy of chemical preservatives is being investigated. A chemical believed to retard the growth of molds in feed must be supported by evidence of less mold growth in feed when the chemical is used than when it is not.

Unfortunately, accurate measurement of mold growth in an amorphous substrate, such as poultry feed, is much more difficult than the measurement of other (such as bacteria) in feed. Most bacteria and yeasts reproduce as single cells or conglomerates comprised of single cells. Therefore, mixing an appropriate diluent with a sample to be analyzed will result in suspension of the cells in the diluent. The diluent can then be diluted further, and the number of viable bacteria or yeasts (indicative of the degree of microbial growth) can be determined by plating the dilutions on an appropriate medium and counting the resulting bacterial colonies. Molds do not reproduce or grow in this fashion in most agricultural commodities. The growth of molds is characterized initially by the development of mycelium. This early stage of mold growth is not visible to the unaided eye. As the mold continues to grow, this mycelium proliferates and forms a continuous and filamentous network throughout the feed. Associated with this mass is also the development of aerial mycelium which serve to project the reproductive spores above the surface of the feed particle. This mycelial mass often becomes an integral part of the individual particles of the commodity being analyzed. Techniques used for the assessment of bacterial or yeast growth are therefore not suitable for assessment of mold growth.

Perhaps the most traditional method for the estimation of mold growth has been the "mold spore count". The premise of this technique is that "the more mold spores in a commodity, the greater the expected mold growth." Mold spores occur singly or as conglomerates, and therefore can be enumerated in a manner similar to that used for the enumeration of bacteria and yeasts. The technical simplicity and the "assumption" that mold spore concentration is indicative of mold growth are the main reasons for the use of this technique to estimate mold growth in feedstuffs. The fallacy in the use of the mold spore count for estimation of mold growth lies in the fact that "sporulation" by molds and "growth" of molds can be independent biological events: a given mold may grow abundantly in feed, but sporulate sparsely. Enumeration of mold spores in this case would lead to the conclusion that only sparse mold growth has occurred in the substrate, when the opposite would be true. Other molds are known to grow sparsely, but produce abundant spores. In this situation also, enumeration of mold spores would lead to erroneous conclusions.

A fundamental concept in microbiology is that microbial growth (including molds) can be measured indirectly by the disappearance of a substrate or the generation of a by-product as a result of growth of the organism. Respirometry has long been used to measure microbial growth in a closed system, usually by measuring oxygen consumption. The Warburg respirometer has been used previously for this purpose, but is not always sufficient because of several limitations. (1) Oxygen consumption is measured by the detection of small changes in pressure within the system, while carbon dioxide is absorbed by the presence of potassium hydroxide in the growth chamber. (2) Only a measurement of oxygen consumption (disappearance of a substrate associated with microbial growth) is capable with the Warburg respirometer. (3) Additionally, since oxygen consumption is determined by slight changes in pressure within the system, extremely stable temperatures are required. (4) In many cases where the actively growing organisms generate heat, the use of the Warburg respirometer is not suitable. (5) Since the Warburg respirometer is a true "closed system", no provisions can be made for the replenishment of oxygen consumed by the microorganisms. Therefore, as oxygen is depleted from the atmosphere within the respirometer, aerobic organisms (i.e. molds) may be unable to maintain optimum growth in an unrestricted state due to the increasing concentration of carbon dioxide and the decreasing concentration of oxygen. (6) Furthermore, the Warburg respirometer requires manual reading of pressure changes within the "closed system"; frequent and periodic measurements are often not practical.

Recently, a unique respirometer ("MICRO-OXYMAX" 20), Columbus Instruments, Columbus, Ohio) has been developed that permits the simultaneous measurement of oxygen consumption and carbon dioxide generation in a "closed system" (See U.S. Pat. No. 4,947,339 and FIG. 1). The air, in up to 20 chambers, is periodically circulated through highly sensitive oxygen and carbon dioxide sensors and then returned to the chambers. The respirometer measures changes in gas concentrations in the chambers with respect to time. Changes in oxygen and carbon dioxide concentrations, coupled with the volume of the chamber and the time elapsed between measurements, permit the calculation of the rate at which oxygen is consumed and the rate at which carbon dioxide is produced. Additionally, the cumulative consumption of oxygen and cumulative production of carbon dioxide can also be determined. The cumulative measurements are indicative of the growth of the mold on the substrate. The rate measurements can be used to determine the rate of mold growth. One useful feature of this particular respirometer is its capability to be programmed to replace or "refresh" the air in each chamber with room air. During long experiments, the concentrations of oxygen and/or carbon dioxide may change significantly from starting concentrations to the extent that the growth rate of the organisms in the chamber may be affected adversely. The user may, in such cases, choose to configure the respirometer to "refresh" each chamber periodically. This maintains optimum levels of oxygen and carbon dioxide equal to those at the onset of the experiment.

Using a combination of valves and switches, the sensors are repetitively and sequentially connected to each of the 20 incubation chambers at user-determined intervals. A microcomputer with specially designed software is used to control the entire system, including the control of measurement of oxygen and carbon dioxide concentrations, calculation of the results, and printing or saving the results to floppy or hard disk. The system also incorporates facilities to assist in sensor calibration and automatic measurement of incubation chamber volumes and barometric pressure.

The "MICRO-OXYMAX" 20 respirometer employs a very stable, single beam, non-dispersive, infrared carbon dioxide sensor that operates over the range of 0–1% carbon dioxide. The oxygen sensor is electrochemical (fuel cell) and has the capability of measuring directly the percentage of oxygen in the chamber atmosphere.

This apparatus is not completely adequate for situations where moisture content of samples is important. No provision is made in this apparatus to control the temperature of the environment surrounding the chambers. Additionally, no provision is made to control the moisture level of the substrate used within each chamber. In the case of moist poultry feed, as the experiment progresses and the atmosphere within each chamber is sampled, water is removed from the atmosphere by the drying column (shown on the left of the system in FIG. 1 is a pump) prior to analysis for specific gas concentrations. During repetitive sampling of the atmosphere within each chamber over time, the samples tend to dehydrate. This dehydration interferes with the normal growth of the mold and often leads to incorrect conclusions.

SUMMARY OF THE INVENTION

Mold growth on a sample is measured by placing the sample in a container that maintains a controlled constant environment that will support rapid mold growth; maintaining the sample at a constant moisture content; initiating mold growth on the sample; and measuring the change of $O_2$ and/or $CO_2$ in the container as a measure of mold growth on the specimen.

BRIEF DESCRIPTION OF THE DRAWINGS

FIG. 2 shows a microbiological incubator and the expansion module. FIG. 3 shows the inside of the incubator and the tube connections.

DESCRIPTION OF THE INVENTION

The present invention is a method and apparatus that overcomes the aforementioned problems heretofore encountered in measuring the growth of mold. This method comprises:

a. placing into a closed container a sample of organic material containing mold spores having a predetermined fixed moisture content that will support rapid growth of mold on said sample;

b. maintaining the environment in said container dark and at a substantially constant temperature and relative humidity that will support rapid mold growth;

c. avoiding condensation of water vapor in said container that changes the moisture content of any part of said sample;

d. avoiding in said container significant change in oxygen and/or carbon dioxide concentration that would impede the mold growth;

e. periodically withdrawing air from said container and determining the concentration of at least one metabolic gas in said air;

f. determining from successive determinations the concentration change of said metabolic gas in said container; and, g. correlating the concentration change of said metabolic gas with the change of mold growth.

Optionally the sample may be inoculated with one or more specific molds and/or mold inhibitors.

The apparatus of the present invention, as more fully described hereinafter, comprises means for accomplishing this method of measuring mold growth.

Figure 1:
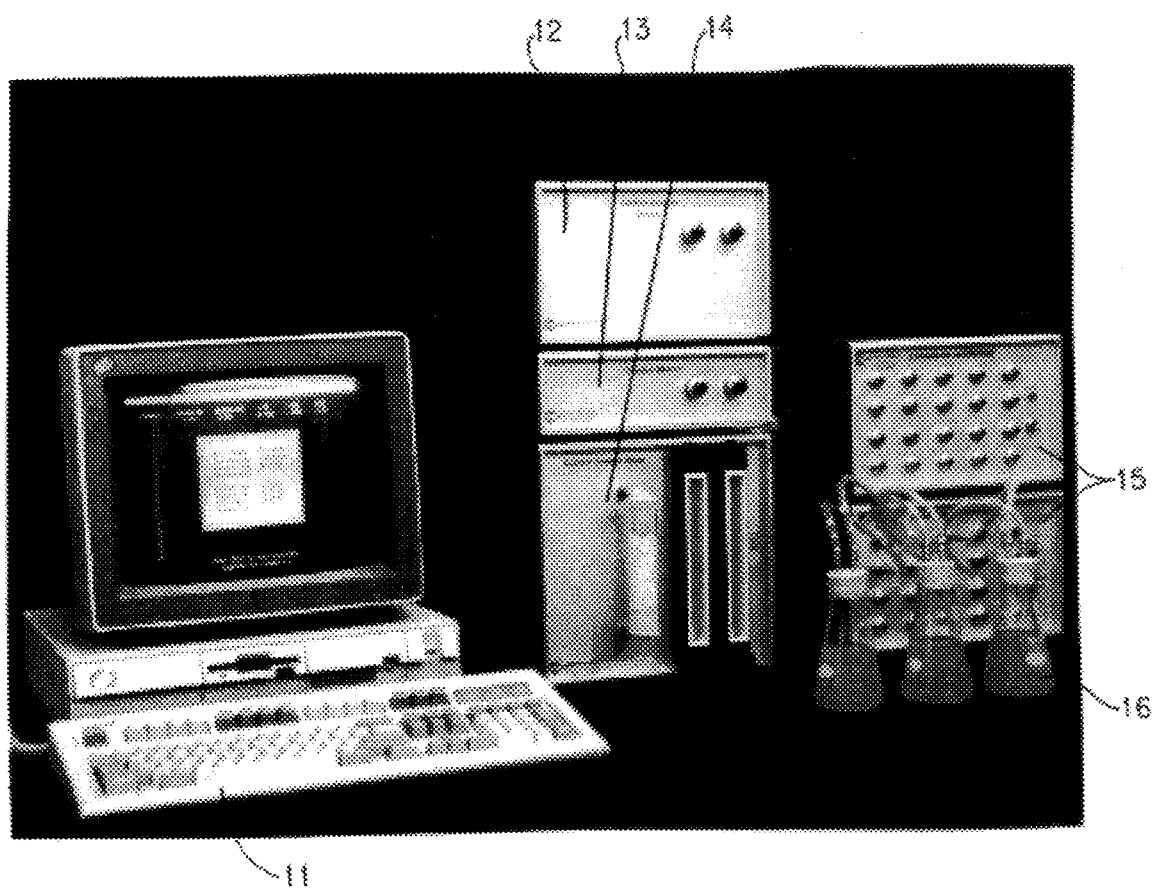
FIG. 1 is a front view of a "MICRO-OXYMAX" 20 showing the hose connections.

In the preferred embodiment of the present invention, a respirometer having the capabilities of the basic "MICRO-OXYMAX" system is used, modified to accomplish the steps and controls of the invention. As shown in FIG. 1, the basic system as bought from the manufacturer comprising a driving computer 11 using appropriate software, a carbon dioxide sensor 12, oxygen sensor 13, system pump 14, and two expansion modules 15. Sample chambers or containers 16 are connected to the expansion modules, which can accommodate many sample chambers. For more details see U.S. Pat. No. 4,947,339, which is incorporated herein in its entirety.

Figure 2:
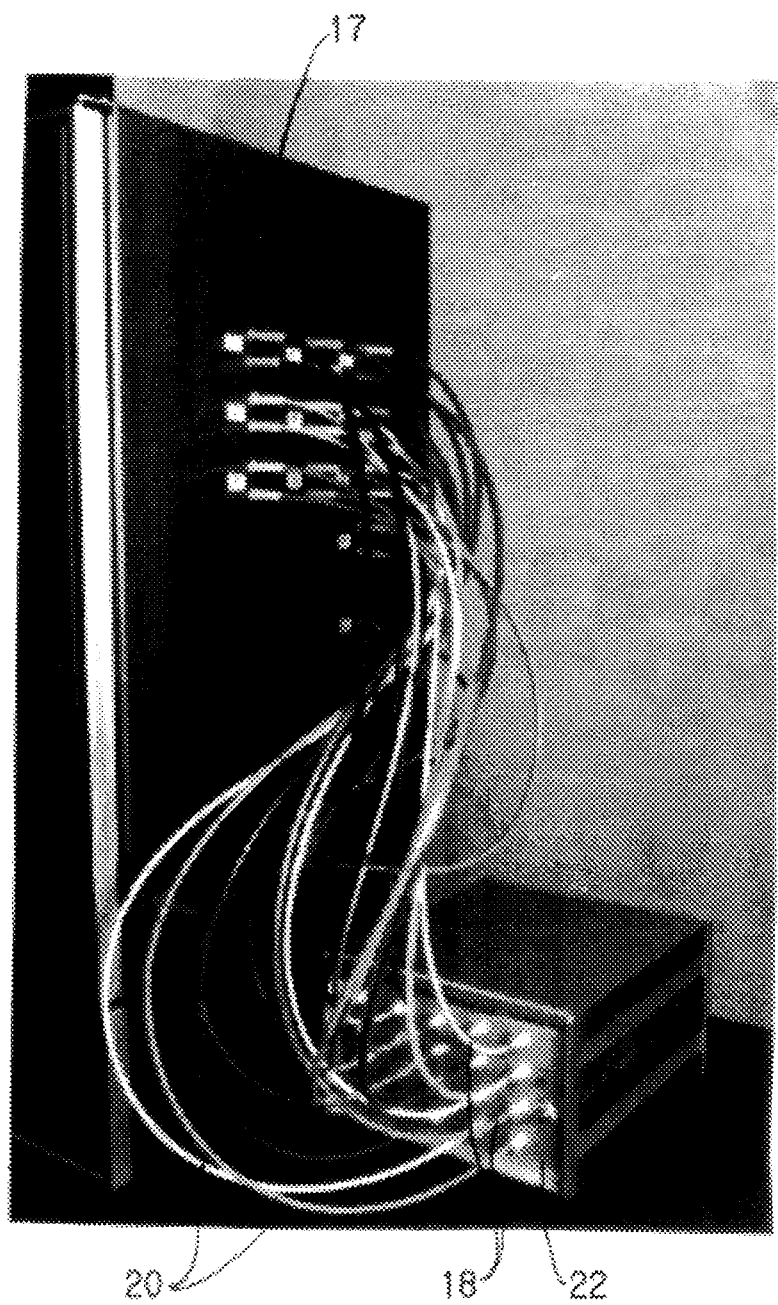
FIGS. 2 and 3 show the "MICRO-OXYMAX" 20 apparatus as used in the present invention.
Figure 3:
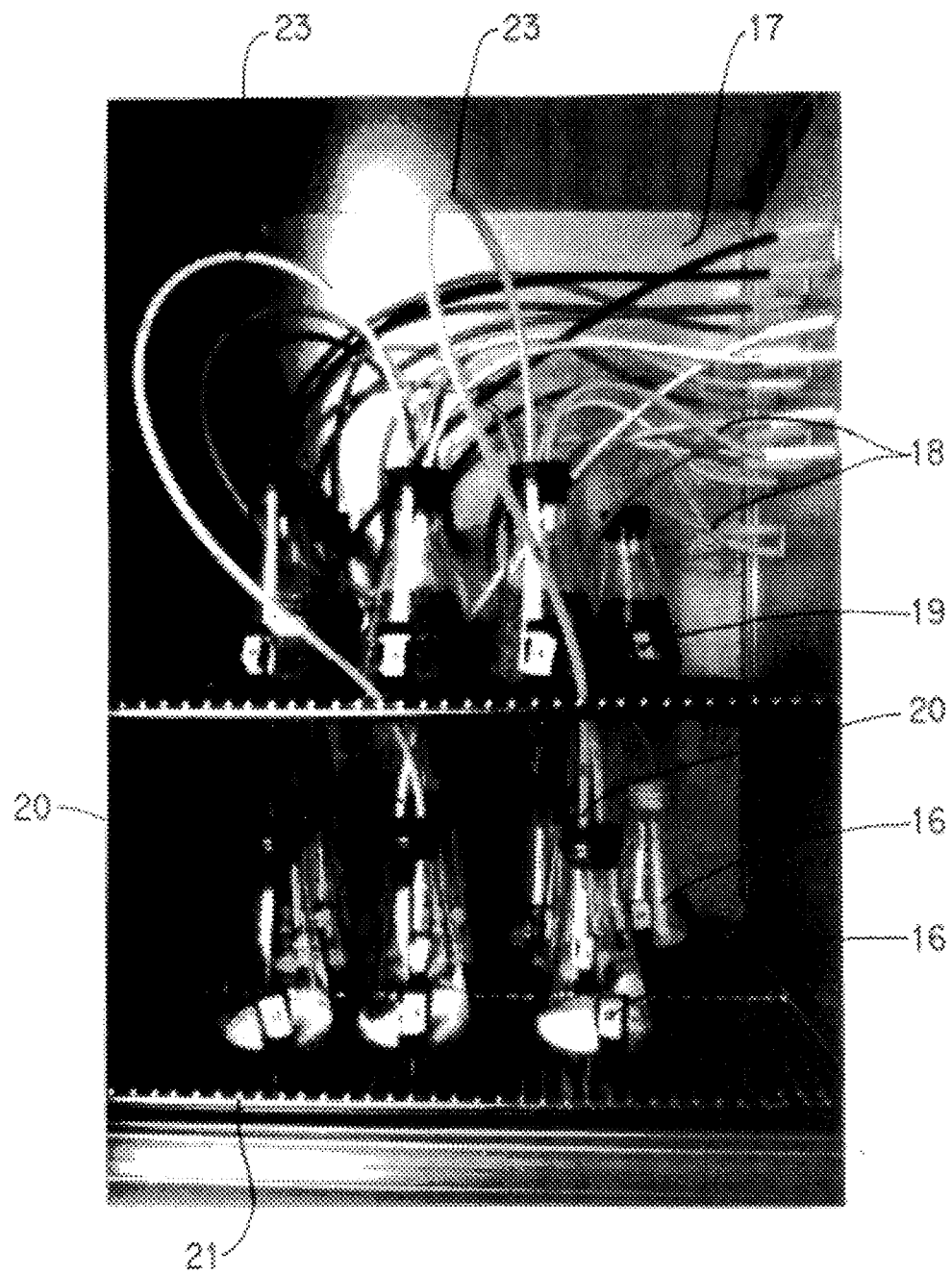

In the apparatus of the present invention, the "MICRO-OXYMAX" is modified as shown in FIGS. 2 and 3. A forced air microbiological incubator 17 is added, in which the sample containers 16 are kept during the test period. The incubator has two tubes per sample container that connect the sample containers 16 to the expansion module.

As shown in FIG. 3, one set of these tubes 18 lead from the explosion module into individual humidifier chambers 19 and are connected by tubes 23 to the sample chambers (or containers), which in turn are connected to an expansion module 22 by sampling tubes 20, through which air samples are taken for measurement of $O_2$ and/or $CO_2$. Thus the chambers containing the samples, such as poultry feed, are connected in line to humidifiers that are between the sample chambers and the expansion modules. The humidifiers are to prevent the samples from dehydrating, that is to humidify the gas going to the samples to near saturation. Each humidifier contains vermiculite and deionized water, or comparable sterilized deionized humidifying agent. All of the chambers and humidifiers are sealed air-tight except for the tubes. The sample containers are placed on an elevated shelf 21 or grating to permit free circulation of air around each container, thereby maintaining a constant uniform temperature around the sample containers. The incubator contains a temperature probe used to monitor a substantially constant temperature in the forced air incubator, and so in the sample chambers.

The enclosed microbiological incubator serves several important functions: (1) accurate control of the temperature during the course of a mold growth test, (2) prevention of the volatilization of water and subsequent condensation thereof in the sample chamber resulting in the buildup of localized high moisture levels in the sample, and (3) minimization of the influence of light, which should to the extent practical be avoided because light can cause photodegredation of the substrate (sample) nutrients and any antifungal agent that might be included in with the sample to be tested.

The humidifiers maintain relatively constant moisture in the sample and in the atmosphere within each sample chamber. Many humidifying systems may be used, typical of which horicultural grade vermiculite (W. R. Grace & Co., Cambridge, Mass.) and deionized water. The water can contain a compound to prevent microbial growth in the moist vermiculite, such as a quaternary ammonium compound. In operation, all air sampled for specific gas is first dried by passing through a drying agent such as anhydrous calcium sulfate (8 mesh, W. A. Hammond Drierite Co., Xenia, Ohio). Repetitive sampling causes dehydration of the sample during the course of the growth rate test. The humidifiers effectively prevent this dehydration process, insuring unrestricted growth of the mold by maintaining a high substantially constant relative humidity in the atmosphere immediately above the substrate in each sample chamber for the entire duration of the test.

This invention has broad applicability to measuring the growth of mold, either a specific mold or a mixture of molds, on samples of any material or shape that support mold growth, such as foods, organic matter generally, and the like. The invention is particularly useful in measuring mold growth on cereal grain, oil seeds, nuts and even silage. The sample may be tested in its natural state, or it may be inoculated with one or more specific mold spores. Also a mold inhibitor may be included to determine its efficacy against molds generally or specifically.

Because of the excellent applicability of the present method and apparatus to mold growth testing on poultry feed, it will be described in detail with respect to poultry feed although the principles apply broadly to mold growth supporting materials.

The quantity of sample, in this case poultry grain feed, in each sample container is important. Too much feed will allow mold growth that results in levels of carbon dioxide produced and oxygen consumed that are too high to be measured accurately by the respirometer. In practice it was found that 10–50 grams of feed in each 250 ml incubation flask is adequate. Other quantities of course would be appropriate for other equipment, certain molds, and test samples. The appropriate quantity ranges are readily determined by simple experimentation.

Particle size also is important. In general uniform particle size of the test substrate is preferred because it gives changes in metabolic gases (which are correlated to mold growth) that are more consistent among replicate sample chambers than are obtainable with nonuniform particle size. The same effect occurs when the particles are relatively small. Thus ground feed grain gives more uniform results than unground feed. Specifically it was found that optimum results were obtained when the feed used in the sample chambers was ground to pass through a sieve with a pore size of 1.0 mm. Of course, the small particle size also ensures ready access of the mold to all nutrients in the feed being tested, thereby insuring unrestricted mold growth.

When a specific mold and/or fungal retardant is to be evaluated, it may be important that the sample be sterilized before inoculation. Of course, if the mold growth of the sample in its natural condition is to be determined, sterilization is not needed. If the sample is to be pulverized before testing, the sterilization should be done after the particle reduction. The primary reason for sterilization is to eliminate all viable organisms in the feed prior to inoculation. Preliminary experimentation indicated that the growth of all aerobic microorganisms will contribute to changes in oxygen consumption and carbon dioxide generation. If a mixed population of microorganisms (i.e., bacteria and molds) are present in the feed, and if a mold inhibitor specifically inhibits the mold population, then the bacteria will undergo rapid growth due to the elimination of the mold competitors. Bacterial growth in the absence of competitive microorganisms (i.e., molds) will result in changes in specific gas concentrations that would indicate no inhibition had occurred when, in fact, the mold population may have been totally inhibited. Additionally, if two or more mold species were present simultaneously in the feed, a given mold inhibitor may be more efficacious toward one species compared to another. Based upon the measurement of specific gas concentrations, one could not discern the species being inhibited from the species not affected by the mold inhibitor.

Moisture level of feed is also a determinant of mold growth in natural substrates. Poultry feed usually has a moisture content of 11.5%–13.5%. At this moisture level, it is generally accepted that the feed will not support mold growth during storage. Recent information indicates that mold growth can occur at moisture levels of approximately 14.0%. However, at this moisture level mold growth is restricted and proceeds very slowly due to low availability of moisture. The commencement of rapid mold growth in feed occurs when a "threshold level" of moisture is exceeded. This relatively high moisture level in feeds can occur as a result of several situations. (1) Feed manufactured from high-moisture ingredients can have a moisture content sufficient to support mold growth. (2) Feed manufactured in a facility where moisture, used for pelleting, is not adequately removed from the feed prior to storage may also contain sufficient moisture to permit rapid mold growth. (3) High moisture levels in feed are known to arise from a phenomenon known as "moisture migration". Moisture migration is the volatilization of water within a feed storage container when environmental temperatures are high (e.g., during the daylight hours). When the environmental temperature decreases (e.g., during hours of darkness), the previously volatilized water vapor condenses and water droplets accumulate in localized areas within a feed storage container. These areas of high water content are usually along the periphery of the feed bin and near the upper surface of the stored feed. Moisture levels at these particular sites routinely exceed 15.0%, and can reach levels of 20% or above. It is in these "microenvironments" that mold growth and mycotoxin formation proceeds at the fastest rate. This is the major source of water vapor condensation in the sample chamber that must be avoided in the practice of the present invention.

By way of example, the above described respirometer apparatus permitted detection of mold growth on poultry feed inoculated with Aspergillus parasiticus at moisture levels as low as 13.06% and showed an accelerate rate of mold growth at increasingly higher moisture levels. Higher moisture levels place a higher demand on any substance added to feed for the inhibition of mold growth. In our experiments, an initial moisture content of at least 17.0% was chosen for the evaluation of natamycin as a mold inhibitor. The success of natamycin in inhibiting mold growth at this moisture level would indicate that inhibition would also occur at lower moisture levels and possibly even higher moisture levels.

The length of incubation is also an important factor. In the poultry industry, the time lapse from feed manufacture to consumption by chickens is approximately 7–14 days. The longer feed is stored, the greater the probability of microbial degradation of the feed, including mold growth and mycotoxin formation. In all experiments with natamycin, a total incubation time of 14 days was used. Basically, in testing mold growth, it is important that a long enough incubation time is allowed to give a meaningful evaluation.

Another important factor is the inoculation level. It is known that inoculation of a substrate (i.e., feed sample) with a relatively low concentration of spores will result in a rather long "lag phase" of the culture. The growth of the mold may also be less compared to a high level of inoculation. For natamycin, an inoculation level (e.g., number of spores/g of feed), the number of spores as low as 5000 spores/gram has been found to be adequate. This level of inoculum insures maximum mold growth over the 14-day incubation period.

As aforementioned, the "MICRO-OXYMAX" apparatus can be set to periodically take air from the sample chambers and determine the concentration of oxygen and/or carbon dioxide (metabolic gases).

The time interval between determining specific gas concentrations in each chamber is also important. If the sampling interval is too short, no appreciable changes may have occurred within each chamber. If the sampling interval is too long, the changes in specific gas concentration could exceed the capability of the respirometer to measure accurately the concentration of each gas. The proper time interval for a particular sample and mold can readily be determined by experiment. For example a 4.0 hour sampling interval has been determined to be appropriate when using 20.0 grams of feed/chamber. Due to the relatively large number of intervals/day (approximately 6), this sampling interval provides information about the initial onset of mold growth in each chamber, accurate to within 4 hours.

Individual samplings of one or more metabolic gases shows the change in concentration since the preceding sample, the delta concentration. This change can be emperically correlated to the rate of mold growth relative to a standard such as a control sample. A series of samplings over a prolonged period of time give a more reliable delta, and so mold growth, measurement than only a few measurements. Also the larger number of samples give an average growth over a selected period of time that relates to actual use situations, such as time of storage.

One of the unique features of the present invention respirometer apparatus is the ability to "refresh" or to exchange the atmosphere within each chamber with ambient air. Refreshment of the chambers is essential because the atmosphere within each chamber can experience a gradual decline in oxygen levels and a gradual increase in carbon dioxide levels with respect to incubation time. As the oxygen decreases and the carbon dioxide increases, the mold will undergo inhibition due to the lack of availability of an essential gas (oxygen) and the accumulation of toxic gas (carbon dioxide). Periodic atmosphere refreshment also permits the mold access to similar levels of oxygen at all stages of the experiment. Furthermore, the carbon dioxide concentration is no more toxic near the end of the experiment than it was during the initial phases of the incubation. The mold will therefore grow at its optimum rate throughout this time.

Excellent results are obtained in testing the growth rate of natamycin on poultry feed when refreshment of the chambers was programmed to occur automatically in all chambers when any one chamber was detected as having a change in either oxygen or carbon dioxide concentration of 0.08% from the initial gas concentrations within the chambers.

In view of these method steps, the apparatus of the present invention comprising:

a. at least one sealable sample container;

b. means for maintaining said sample container in a dark environment at substantially constant selected temperature and relatively humidity inside the container during the test period;

c. means for avoiding condensation of water vapor in said container during testing;

d. means for refreshing the air in the containers when sealed during testing to limit changes in metabolic gases within the container;

e. means for withdrawing samples of air periodically from said sample container when sealed during testing, and f. means for measuring the concentration of at least one metabolic gas in said samples of air.

In the following examples the preferred apparatus of the present invention comprising "MICRO-OXYMAX" apparatus modified as above-described.

EXAMPLE 1

This example demonstrates measurements of growth of aflatoxin producing Aspergillus parasiticus on poultry feed treated with natamycin fungal growth retardant.

A commercial broiler starter ration, free of all medications (Table 1), was obtained from a commercial poultry feed mill. The feed was finely ground in a laboratory grinder to a particle size of approximately 1 $mm^3$. The feed was then sterilized (121° C. for 15 minutes). The moisture content was determined by drying a sample in a forced draft oven at 135° C. for 2 hours (AOAC Method 930.15). A sufficient quantity of sterile deionized water was added to 1.0 kg of the feed and mixed thoroughly to attain a theoretical moisture content of 17.0%. The actual final moisture content was then determined (AOAC Method 930.15). Five-200 g aliquots of the moistened feed were transferred to each of five 2800 ml Fernbach flasks.

TABLE 1

COMPOSITION AND CALCULATED ANALYSIS OF BROILER CHICKEN FEED USED AS A SUBSTRATE FOR FUNGAL GROWTH RETARDATION STUDIES WITH NATAMYCIN

| Ingredient | % | lb/ton |
|---|---|---|
| Ground yellow corn | 57.31 | 1146.2 |
| Soybean meal, dehulled (49.0% protein) | 33.48 | 669.6 |
| Poultry fat | 3.15 | 63.0 |
| Poultry by-product meal | 3.00 | 60.0 |
| Defluorinated phosphate | 1.54 | 30.8 |
| Limestone | 0.79 | 15.8 |
| Vitamin premix[1] | 0.28 | 5.6 |
| Salt | 0.21 | 4.2 |
| D,L Methionine (98%) | 0.19 | 3.8 |
| Trace Mineral Mix[2] | 0.05 | 1.0 |

| Calculated composition | |
|---|---|
| Metabolizable energy, kcal/kg | 3100 |
| Protein, % | 23.00 |
| Calcium, % | 1.00 |
| Phosphorus, total % | 0.72 |
| Phosphorus, available % | 0.48 |
| Methionine + Cystine, % | 0.93 |
| Lysine, % | 1.25 |
| Sodium, % | 0.20 |

[1]Vitamin premix provides (per kg/diet): vitamin A, 5500 IU; vitamin D3, 1100 ICU; vitamin E, 11 IU; riboflavin, 4.4 mg; calcium pantothenate, 12 mg; nicotinic acid, 44 mg; choline chloride, 220 mg; vitamin B12, 6.6 mcg; vitamin B6, 2.2 mg; menadione, 1.1 mg (as MSBC); folic acid, 0.55 mg; D-biotin, 0.11 mg; thiamine, 2.2 mg (as thiamine monohydrate); ethoxyquin, 125 mg; selenium, 0.3 mg (as sodium selenite).
[2]Trace mineral mix provides (ppm of diet): Manganese, 60; Zinc, 50; Iron, 30; Copper, 5; Iodine, 1.5.

A spore suspension of *Aspergillus parasiticus*, NRRL 2999 was prepared by adding 9.0 ml of sterile diluent (0.005% "Triton" X-100 in water) to a mature slant culture of the mold. The surface of the slant was scraped gently with a sterile microbiological loop to facilitate spore release from the mycelium. The concentration of viable spores in the suspension was determined by standard dilution and pour-plate methodology using Saborauds dextrose agar as the plating medium. An appropriate volume of the suspension was added to each aliquot of feed to attain $5-8 \times 10^3$ spores/g. Following thorough mixing, weighed quantities of a natamycin premix were added to each 200 gram aliquot to attain concentrations of 0 (CONTROL), 5, 10, 15, and 20 grams of natamycin/ton of feed. The feed was remixed and 20 gram samples of each of the treated feeds were placed in 250 ml wide mouth Erlenmeyer flasks that served as chambers for incubation in the respirometer. Four replicate flasks were prepared for each level of natamycin.

All flasks were sealed with rubber stoppers and pre-incubated for 48 hours at 30° C. After this initial pre-incubation period, all flasks were placed in a microbiological incubator at 30° C., and connected to a respirometer ("MICRO-OXYMAX" 20, Columbus Instruments, Columbus, Ohio). Each flask chamber was fitted with a humidifier to insure a stable feed moisture content throughout the duration of the experiment. Measurements of oxygen consumption and carbon dioxide production were determined every 4 hours for 288 hours (12 days). All data were calculated as cumulative oxygen consumption and cumulative carbon dioxide production.

The availability of moisture is perhaps the most critical factor relating to mold growth on a particular substrate. The initial moisture content of the feed used was determined to be 17.00%. This moisture level, in combination with an optimum temperature (30° C.) for growth of *A. parasiticus* in the presence of a suitable substrate, insured prolific mold growth.

All cultures were incubated for approximately 2 days prior to commencing respirometry. Consequently, the initial respirometric measurements (146 hours post-inoculation) reflect the status of the the onset after the onset of mold growth.

At 146 hours post-inoculation, there was no significant difference in cumulative carbon dioxide production between the CONTROL and 5 g/ton cultures. However, significantly lower levels of carbon dioxide production were noted between the CONTROL cultures and the 10 g/ton, 15 g/ton and 20 g/ton cultures. This is a reflection of the antifungal activity of natamycin exhibited during the 6-day "pre-incubation" of the cultures. At 163.5 hours post-inoculation, significant differences in cumulative carbon dioxide production between CONTROL cultures and cultures containing all four levels of natamycin were observed. These differences continued to be significant throughout the remainder of this Example.

With regard to oxygen consumption at the same intervals, no significant differences were noted at 146 hours post-inoculation between any of the treatments. At 163.5 hours post-inoculation, there were significant differences in oxygen consumption between the control cultures and all cultures containing natamycin. All natamycin cultures exhibited significantly lower levels of oxygen consumption relative to the control cultures throughout 238.5 hours post-inoculation. For the remainder of this Example, the CONTROL and 5 g/ton cultures were not significantly different. However, the 10, 15 and 20 g/ton concentrations of natamycin reduced oxygen consumption significantly in relation to the CONTROL culture.

Based upon the significantly lower cumulative carbon dioxide production and cumulative oxygen consumption in moist poultry feed cultures inoculated with *Aspergillus parasiticus*, it can be concluded that natamycin retards the growth of this toxigenic mold. Furthermore, this mold-retarding activity was evident as early as 146 hours post-inoculation. Additionally, the carbon dioxide production data indicate that 5 g/ton of natamycin or more is sufficient to significantly retard mold growth during a 16-day period. The oxygen consumption data indicate that a concentration of no less than 10 g/ton of natamycin is required to decrease significantly the growth of this mold during the same amount of time.

EXAMPLE 2

This Example was conducted in a manner similar to Example 1, with the following exceptions: (1) the initial moisture concentration in the feed was 17.38%, (2) the initial inoculum was 5000 spores/g, and (3) the incubation period was reduced to approximately 24 hours. All other experimental conditions were the same as those in Example 1. Also, the time period between inoculation of the moist poultry feed with *A. parasiticus* and commencement of respirometric measurements was less in Example 2 than in Example 1. Consequently, initial measurements of cumulative carbon dioxide production were not significantly different between the various treatments. The mold retarding activity of natamycin was first evident at 98.5 hours post-inoculation. At this time, all cultures treated with natamycin exhibited significantly lower levels of carbon dioxide production compared to the CONTROL culture. This effect of natamycin persisted through 313 hours post-inoculation. At 340.5 hours post-inoculation, only the cultures containing 15 and 20 g/ton concentrations of natamycin were significantly different then the CONTROL culture.

Similar results were obtained from measurements of cumulative oxygen consumption. At both 46.5 and 72 hours post-inoculation, no significant differences were noted among the various treatments. However, at 98.5 hours post-inoculation, cumulative oxygen consumption in all natamycin cultures was significantly lower than in the CONTROL culture. These differences persisted throughout 291 hours post-inoculation. At 313 and 340.5 hours post-inoculation, cultures containing 10 g/ton or greater consumed significantly lower levels of oxygen than the CONTROL cultures.

Based upon cumulative carbon dioxide production and cumulative oxygen consumption in moist poultry feed inoculated with A. parasiticus, it can again be concluded that natamycin retards the growth of this toxigenic mold. The retardation of mold growth was evident in this Experiment as early as 98.5 hours post-inoculation. The failure to note a significant effect of natamycin on either carbon dioxide production or oxygen consumption during the first 3 days of respirometry is most likely a reflection of the time required for hydration of the mold spores, followed by germination of the spores and hyphal development. During these initial phases, the spores respire, as reflected by carbon dioxide production and oxygen consumption during the first 3 days; however, no marked hyphal development occurs until after the first 3 days. Not until this hyphal development occurs does natamycin exert its mold retarding activity. This is due to the known mechanism of action of natamycin: natamycin interferes with hyphal growth by interacting with hyphal cell wall sterols. Based upon carbon dioxide production, 15 g/ton of natamycin or more is required to significantly decrease mold growth for 14 days. Based upon oxygen consumption, no less than 10 g/ton of natamycin is required to retard mold growth for the same amount of time.

A comparison of Example 1 and 2 indicates that growth of A. parasiticus in moist poultry feed is retarded by concentrations of natamycin between 5–15 g/ton. In both Examples, 10 g/ton resulted in a significant reduction in cumulative oxygen consumption. The minimal concentration of natamycin required to retard mold growth, based on carbon dioxide production, was 5 g/ton in Example 1 and 15 g/ton in Example 2. It is concluded that a concentration of 10 g/ton would be appropriate to insure significant reductions in mold growth in moist poultry feed.

While the examples deal primarily with the efficacy of fungal retardants, measurements of natural mold growth are made in the same manner on organic substrates including bread and other foods, leather, and moist cellulosic materials. Mold growth measurements using other fungal retardants, including nystatin, propionic acid, and its salts, are also similarly made. Also measurements made in the same manner on untreated and fungal retardant treated organic substrates for the growth of other molds including Fusarium sps or Pennicillum sps.

EXAMPLE 3

In recent years, Fusarium moniliforme has attained importance as a contaminant of feedstuffs. Surveys of poultry feeds over the past 2 decades have revealed that F. moniliforme is the most prevalent species of Fusarium found in poultry feeds. F. moniliforme has been found to produce a group of toxins, collectively referred to as the fumonisins. The fumonisins possess a wide range of toxicities, including carcinogenic potential. Due to the widespread occurrence F. moniliforme, the toxicity of its metabolites, and the disease-causing potential of these metabolites in poultry, this particular mold was included in this evaluation of natamycin for possible mold retarding activity.

A commercial broiler starter ration, free of all medications (Table 1), was obtained from a commercial poultry feed mill. The feed was finely ground in a laboratory grinder to a particle size of approximately 1 $mm^3$. The feed was then sterilized (121° C. for 15 minutes). The moisture content was determined by drying a sample in a forced-draft oven at 135° C. for 2 hours (AOAC Method 930.15). A sufficient quantity of sterile deionized water was added to 1.0 kg of the feed and mixed thoroughly to attain a theoretical moisture content of 17.0%. The actual final moisture content was then determined (AOAC Method 930.15). Five 200 g aliquots of moistened feed were transferred to each of five 2800 ml Fernbach flasks.

A spore suspension of Fusarium moniliforme, NRRL 5806 was prepared by adding 9.0 ml of sterile diluent (0.005% "Triton" X-100 in water) to a mature slant culture of the mold. The surface of the slant was scraped gently with a sterile microbiological loop to facilitate spore release from the mycelium. The concentration of viable spores in the suspension was determined by standard dilution and pour-plate methodology using Saborauds dextrose agar as the plating medium. An appropriate volume of the suspension was added to each aliquot of feed to attain $5.0 \times 10^3$ spores/g. Following thorough mixing, weighed quantities of a natamycin premix were added to each 200 gram aliquot to attain concentrations of 0 (CONTROL), 5, 10, 15, and 20 grams of natamycin/ton of feed. The feed was remixed and 20 gram samples of each of the treated feeds were placed in 250 ml wide mouth Erlenmeyer flasks that served as chambers for incubation in the respirometer. Four replicate flasks were prepared for each level of natamycin.

All flasks were sealed with rubber stoppers and pre-incubated for approximately 40 hours at 30° C. After this initial pre-incubation period, all flasks were placed in a microbiological incubator at 30° C. and connected to the respirometer ("MICRO-OXYMAX" 20, Columbus Instruments, Columbus, Ohio). Each flask (chamber) was fitted with a humidifier to insure a stable feed moisture content throughout the duration of the experiment. Measurements of oxygen consumption and carbon dioxide production were determined every 4 hours for 364 hours (15 days). All data were calculated as cumulative oxygen consumption and cumulative carbon dioxide production.

The availability of moisture is perhaps the most critical factor relating to mold growth on a particular substrate. The initial moisture content of the feed used in this experiment was determined to 17.70%. This moisture level, in combination with a suitable temperature (30° C.) for growth of F. moniliforme in the substrate, insured prolific mold growth.

At 46 and 71.5 hours post-inoculation, there were no significant differences in cumulative carbon dioxide between any of the cultures. At 93 hours post-inoculation, all cultures containing natamycin produced significantly lower carbon dioxide levels than the CONTROL culture. This relationship persisted through 314 hours post-inoculation.

With regard to oxygen consumption at the same intervals, no significant differences were noted at either 46 or 71.5 hours post-inoculation. However, at 93 hours post-inoculation, cultures containing natamycin concentrations of 10 g/ton or greater consumed significantly lower levels of oxygen than the CONTROL culture. At 117.5 hours post-inoculation, all natamycin cultures were significantly different from the CONTROL culture. This relationship persisted through 286.5 hours post-inoculation.

Based upon the significantly lower cumulative carbon dioxide production and cumulative oxygen consumption in moist poultry feed inoculated with *F. moniliforme*, it can be concluded that natamycin retards the growth of this toxigenic mold in poultry feed. Furthermore, this mold retarding activity was evident as early as 93 hours post-inoculation. Additionally, the carbon dioxide product and oxygen production indicate that 5 g/ton of natamycin or more is sufficient to significantly retard the growth of this species of Fusarium.

EXAMPLE 4

The effects of natamycin on oxygen consumption and carbon dioxide production by *Penicillium rubrum* NRLL 3290 in broiler chicken feed is demonstrated by this example of mold growth rate measurements in accordance with the present invention.

*Penicillium rubrum* is recognized as a common contaminant in feedstuffs such as corn and wheat, and in complete feeds. The primary toxin produced by *P. rubrum* is rubratoxin B. Rubratoxin B is known to cause a fatal hemorrhagic syndrome in poultry, which is characterized by congestion of the visceral organs. The LD50 for rubratoxin in chickens has been estimated to be 4.0 mg/kg. Based upon the high probability for *P. rubrum* to contaminate feedstuffs used in the poultry industry, and the potential toxicosis resulting from formation of rubratoxin, *P. rubrum* was included in this investigation to assess the mold retarding activity of natamycin in moist poultry feed.

A commercial broiler starter ration, free of all medications (Table 1), was used. The feed was finely ground in a laboratory grinder to a particle size of approximately 1 $mm^3$. The feed was then sterilized (121° C. for 15 minutes). The moisture content was determined by drying a sample in a forced-draft oven at 135° C. for 2 hours (AOAC Method 930.15). A sufficient quantity of sterile deionized water was added to 1.0 kg of the feed and mixed thoroughly to attain a theoretical moisture content of 17.0%. The actual final moisture content was then determined (AOAC Method 930.15). Five 200 g aliquots of moistened feed were transferred to each of five 2800 ml Fernbach flasks.

A spore suspension of *Penicillium rubrum*, NRRL 3209 was prepared by adding 9.0 ml of sterile diluent (0.005% "Triton" X-100 in water) to a mature slant culture of the mold. The surface of the slant was scraped gently with a sterile microbiological loop to facilitate spore release from the mycelium. The concentration of viable spores in the suspension was determined by standard dilution and pour-plate methodology using Saborauds dextrose agar as the plating medium. An appropriate volume of the suspension was added to each aliquot of feed to attain $5.0 \times 10^3$ spores/g. Following thorough mixing, weighed quantities of a natamycin premix were added to each 200 gram aliquot to attain concentrations of 0 (CONTROL), 5, 10, 15, and 20 grams of natamycin/ton of feed. The feed was remixed and 20 gram samples of each of the treated feeds were placed in 250 ml wide mouth Erlenmeyer flasks that served as chambers for incubation in the respirometer. Four replicate flasks were prepared for each level of natamycin.

All flasks were sealed with rubber stoppers and pre-incubated for approximately 115 hours at 30° C. After this initial pre-incubation period, all flasks were placed in a microbiological incubator at 30° C. and connected to the respirometer ("MICRO-OXYMAX" 20, Columbus Instruments, Columbus, Ohio). Each flask (chamber) was fitted with a humidifier to insure a stable feed moisture content throughout the duration of the experiment. Measurements of oxygen consumption and carbon dioxide production were determined every 4 hours for 340 hours (14 days). All data were calculated as cumulative oxygen consumption and cumulative carbon dioxide production.

The availability of moisture is perhaps the most critical factor relating to mold growth on a particular substrate. The initial moisture content of the feed used in this Experiment was determined to be 17.20%. This moisture level, in combination with a suitable temperature (30° C.) for growth of *Penicillium rubrum* in the substrate, insured the proliferation of this mold. Penicillium, as a genus, is known to require somewhat higher moisture levels and water activities, compared to other toxigenic genera such as Aspergillus and Fusarium. Although Aspergillus and Fusarium can exhibit rapid growth at a moisture level of approximately 17%, this same moisture level does not have an equivalent rate of growth for most species of Penicillium.

No significant differences in cumulative carbon dioxide production were observed for this species of Penicillium in all cultures until 219 hours post-inoculation. At all subsequent time intervals, no significant differences in cumulative carbon dioxide were noted. The failure of the presence of natamycin in the feed to show a consistent and significant reduction in cumulative carbon dioxide production may have been due to the low rate of growth of this particular mold. For example, 76.3 ml of total carbon dioxide was produced by *Aspergillus parasiticus* compared to only 16.4 ml of total carbon dioxide by *P. rubrum* over an equivalent period of time. As explained previously, species of Penicillium do not grow as rapidly as those of Aspergillus and Fusarium grown in the same substrate containing similar moisture levels.

The difference between carbon dioxide production and oxygen consumption in this experiment points to the necessity of simultaneous measurement of both of these gases for accurate assessment of the mold retarding activity of natamycin, and any other compounds used for similar purposes. Furthermore, the evaluation of such compounds must take into account the differences in optimal moisture level required for mold growth of different genera and species.

While the above examples deal primarily with the efficacy of fungal retardants, measurements of natural mold growth are made in the same manner on organic substrates including bread and other foods, leather, and moist cellulosic materials and the like. Mold growth measurements using other fungal retardants including nystatin and the like are also similarly made. Also measurements made in the same manner on untreated and fungal retardant treated organic substrates for the growth of other molds.

What is claimed:

1. A method for determining mold growth on feed, the method comprising:
   (1) placing into a closed container a sample of feed containing mold spore, the sample having a moisture content that will support the growth of mold on the sample;
   (2) maintaining a substantially constant temperature and a substantially constant relative humidity that will support rapid mold growth in the container, wherein a uniform moisture content is maintained throughout the sample;
   (3) periodically refreshing the atmosphere in the container so that concentrations of oxygen and concentrations of carbon dioxide that would impede mold growth are avoided;

(4) periodically withdrawing air from the container and measuring the concentration of at least one metabolic gas, the metabolic gas selected from the group consisting of oxygen and carbon dioxide;

(5) determining from successive measurements a concentration change of at least one metabolic gas in the container; and (6) correlating the concentration change with the rate of mold growth.

2. The method of claim 1 in which the feed is poultry feed ground to pass through a sieve with a pore size of 1.0 mm.

3. The method of claim 1 in which the relative humidity is greater than 13.06%.

4. The method of claim 1 additionally comprising, before step (1), inoculating the sample feed with spores of a specific mold.

5. The method of claim 1 additionally comprising, before step (1), treating the sample with a fungal retardant.

6. The method of claim 5 in which the fungal retardant is selected from the group consisting of natamycin, nystatin, and propionic acid and its fungicidal salts.

7. The method of claim 5 in which the feed is poultry feed ground to pass through a sieve with a pore size of 1.0 mm.

8. The method of claim 1 additionally comprising, before step (1), (A) sterilizing the sample;

(B) inoculating the sample with spores of a specific mold; and (C) treating the sample with a fungal retardant;

wherein step (A) is carried out before steps (B) and (C).

9. The method of claim 8 in which the fungal retardant is selected from the group consisting of natamycin, nystatin, and propionic acid and its fungicidal salts.

10. The method of claim 8 in which the feed is poultry feed ground to pass through a sieve with a pore size of 1.0 mm.

11. The method of claim 10 in which the fungal retardant is selected from the group consisting of natamycin, nystatin, and propionic acid and its fungicidal salts.

12. The method of claim 10 in which the relative humidity is greater than 13.06%.

13. A method for determining mold growth on feed, the method comprising:

(1) placing into a closed container a sample of feed containing mold spore, the sample having a moisture content that will support the growth of mold on the sample;

(2) maintaining a substantially constant temperature and a substantially constant relative humidity that will support rapid mold growth in the container, wherein a uniform moisture content is maintained throughout the sample;

(3) periodically refreshing the atmosphere in the container so that concentrations of oxygen and concentrations of carbon dioxide that would impede mold growth are avoided;

(4) periodically withdrawing a sample of the atmosphere from the container and measuring the concentration of at least one metabolic gas, the metabolic gas selected from the group consisting of oxygen and carbon dioxide;

(5) determining from successive measurements a concentration change of at least one metabolic gas in the container; and (6) correlating empirically the concentration change to the rate of mold growth relative to a control sample.

14. The method of claim 13 wherein the feed is poultry feed ground to pass through a sieve with a pore size of 1.0 mm.

15. A method for determining mold growth on feed, the method comprising:

(1) placing into a closed container a sample of feed containing mold spore, the sample having a moisture content that will support the growth of mold on the sample;

(2) maintaining a substantially constant temperature and a substantially constant relative humidity that will support rapid mold growth in the container, wherein a uniform moisture content is maintained throughout the sample;

(3) periodically refreshing the atmosphere in the container so that concentrations of oxygen and concentrations of carbon dioxide that would impede mold growth are avoided;

(4) periodically withdrawing a sample of the atmosphere from the container and measuring the concentration of at least one metabolic gas, the metabolic gas selected from the group consisting of oxygen and carbon dioxide;

(5) calculating from successive measurements the cumulative change in at least one metabolic gas.

16. The method of claim 15 wherein successive measurements of carbon dioxide concentration are calculated as cumulative carbon dioxide production.

17. The method of claim 15 wherein successive measurements of oxygen concentration are calculated as cumulative oxygen consumption.

18. The method of claim 15 wherein the feed is poultry feed ground to pass through a sieve with a pore size of 1.0 mm.

19. The method of claim 18 wherein successive measurements of carbon dioxide concentration are calculated as cumulative carbon dioxide production and successive measurements of oxygen concentration are calculated as cumulative oxygen consumption.

* * * * *